United States Patent
Macke et al.

(10) Patent No.: US 10,730,167 B2
(45) Date of Patent: Aug. 4, 2020

(54) DISPOSABLE SURGICAL SCREWDRIVER

(71) Applicant: Zimmer, Inc., Warsaw, IN (US)

(72) Inventors: Jacob Macke, Warsaw, IN (US); Steven Conrad, Albion, IN (US)

(73) Assignee: Zimmer, Inc., Warsaw, IN (US)

( * ) Notice: Subject to any disclaimer, the term of this patent is extended or adjusted under 35 U.S.C. 154(b) by 200 days.

(21) Appl. No.: 16/036,397

(22) Filed: Jul. 16, 2018

(65) Prior Publication Data

US 2019/0022833 A1 Jan. 24, 2019

Related U.S. Application Data

(60) Provisional application No. 62/534,389, filed on Jul. 19, 2017.

(51) Int. Cl.
*B25B 13/46* (2006.01)
*B25B 15/04* (2006.01)
*A61B 17/88* (2006.01)
*A61B 17/70* (2006.01)

(52) U.S. Cl.
CPC ........ *B25B 13/463* (2013.01); *A61B 17/8875* (2013.01); *B25B 15/04* (2013.01); *A61B 17/7076* (2013.01)

(58) Field of Classification Search
CPC ...... B25B 13/462; B25B 13/463; B25B 15/04
See application file for complete search history.

(56) References Cited

U.S. PATENT DOCUMENTS

| | | | |
|---|---|---|---|
| 210,942 A | 12/1878 | Gay | |
| 2,396,040 A | 3/1946 | Darling | |
| 4,249,435 A | 2/1981 | Villeneuve et al. | |
| 5,526,724 A | 6/1996 | Bruggeman | |
| 7,127,955 B2 * | 10/2006 | Bondhus | B25B 15/02 73/862.23 |
| 9,108,304 B2 * | 8/2015 | Lai | B25B 13/463 |
| 9,421,675 B2 * | 8/2016 | Yu | B25B 23/141 |
| 9,446,507 B2 * | 9/2016 | Nino | A61B 17/8875 |
| 10,195,724 B2 * | 2/2019 | Nino | A61B 17/8875 |
| 10,207,398 B2 * | 2/2019 | Ma | B25B 13/463 |
| 10,335,930 B2 * | 7/2019 | Cutler | B25B 13/465 |
| 2017/0106505 A1 | 4/2017 | Chang | |

FOREIGN PATENT DOCUMENTS

| | | |
|---|---|---|
| EP | 0003896 A1 | 9/1979 |
| EP | 0978355 B1 | 2/2000 |
| WO | WO-0025986 A2 | 5/2000 |

* cited by examiner

*Primary Examiner* — David B. Thomas

(74) *Attorney, Agent, or Firm* — Schwegman Lundberg & Woessner, P.A.

(57) ABSTRACT

A ratcheting driver can be configured to selectively transmit a torque to a fastener. The driver can include a handle, a geared body, and a shaft. The handle can include a housing, a pawl, and a biasing element. The housing can include a central bore and a shaft bore extending through a distal portion of the housing. The pawl can extend radially inward from the housing into the central bore. The biasing element can engage the housing. The geared body can be rotatably engageable with the pawl to allow rotation of the geared body relative to the handle in a first direction and to limit rotation of the geared body relative to the handle in a second direction, where the biasing element can be engageable with the geared body to bias the geared body distally.

20 Claims, 9 Drawing Sheets

DISPOSABLE SURGICAL SCREWDRIVER

CLAIM OF PRIORITY

This application claims the benefit of U.S. Provisional Patent Application Ser. No. 62/534,389, filed on Jul. 19, 2017, the benefit of priority of which is claimed hereby, and which is incorporated by reference herein in its entirety.

BACKGROUND

A hand driver is a tool designed to deliver torque to a fastener, such as a screw or bolt. Hand drivers often include a graspable handle configured to transfer torque down a shaft coupled to the handle. A distal termination of the shaft can include a tool interface, such as cross-recess, standard, hexagonal, configured to mate with a head of the fastener or other instrument. The torque can be transferred down the shaft to the tool interface and into the fastener, which can be driven into a working substrate, such as bone or a rigid coupler. Hand drivers are commonly used in surgical procedures to install fasteners to retain plates and prostheses.

Overview

The following, non-limiting examples, detail certain aspects of the present subject matter to solve the challenges and provide the benefits discussed herein, among others.

Example 1 is a ratcheting driver configured to selectively transmit a torque to a fastener, the driver comprising: a handle comprising: a housing including a central bore and a shaft bore extending through a distal portion of the housing; a pawl extending radially inward from the housing into the central bore; and a biasing element engaging the housing; a geared body rotatably engageable with the pawl to allow rotation of the geared body relative to the handle in a first direction and to limit rotation of the geared body relative to the handle in a second direction, the biasing element engageable with the geared body to bias the geared body distally, the geared body proximally translatable within the handle to engage the handle to limit rotation of the geared body relative to the handle in the first direction and the second direction; and a shaft extendable through the shaft bore and coupleable to the geared body and rotatable therewith, the shaft configured to interface with a fastener.

In Example 2, the subject matter of Example 1 optionally includes wherein the pawl is formed into a radially inner portion of the housing.

In Example 3, the subject matter of any one or more of Examples 1-2 optionally include the handle further comprising: a cap secured to the housing and extending distally into the central bore, the cap engageable with the geared body when the geared body is proximally translated, the cap comprising: a cap bore configured to receive the biasing element therein; and a cap boss disposed in the cap bore and extending distally, the cap boss extending into the biasing element to limit non-axial movement of the biasing element relative to the cap.

In Example 4, the subject matter of any one or more of Examples 1-3 optionally include the geared body further comprising: a geared body groove configured to receive the biasing element therein; and a body boss disposed in the geared bore and extending proximally, the body boss extending into the biasing element to limit non-axial movement of the biasing element relative to the geared body.

In Example 5, the subject matter of any one or more of Examples 1-4 optionally include the handle further comprising: a cap secured to the housing and extending distally into the central bore, the cap comprising: a cap tooth extending distally from the cap to engage the geared body when the geared body is proximally translated.

In Example 6, the subject matter of Example 5 optionally includes the geared body further comprising: a geared body tooth extending proximally from the geared body to engage the cap when the geared body is proximally translated and to engage the cap tooth to prevent the geared body from rotating relative to the handle.

In Example 7, the subject matter of Example 6 optionally includes wherein: the geared body tooth includes a plurality of geared body teeth, each geared body tooth including radially extending edges.

In Example 8, the subject matter of any one or more of Examples 1-7 optionally include the geared body further comprising: a guide extending radially from a distal portion of the geared body to engage a radially internal wall of the body of the handle to prevent non-axial translation of the geared body.

In Example 9, the subject matter of any one or more of Examples 1-8 optionally include a collar coupleable to proximal portion of the handle and rotatable relative to the handle and the shaft.

In Example 10, the subject matter of any one or more of Examples 1-9 optionally include wherein the pawl is coupleable to the housing.

In Example 11, the subject matter of any one or more of Examples 1-10 optionally include wherein: the central bore further comprises a distal portion having a distal bore diameter and a proximal portion having a proximal bore diameter that is larger than the distal bore diameter; and the geared body further comprises a distal portion having a distal geared body diameter that is smaller than the distal bore diameter, and a proximal portion having a proximal geared body diameter that is larger than the distal geared body diameter, larger than the distal bore diameter and smaller than the proximal bore diameter so that distal translation of the geared body is limited by contact between the proximal portion of the geared body and an undercut formed between distal portion and proximal portion of the central bore.

Example 12 is a ratcheting driver configured to selectively transmit a torque to a fastener, the driver comprising: a housing including a central bore; a plurality of pawls extending radially from the housing into the central bore; a biasing element engaging the housing; a geared body translatable within the housing between a first position and a second position and rotatably engageable with the plurality of pawls to allow rotation of the geared body relative to the housing in a first direction and to limit rotation of the geared body relative to the housing in a second direction when the geared body is in the first position, the biasing element engageable with the geared body to bias the geared body to the first position, and the geared body engageable with the housing to limit rotation of the geared body relative to the housing in the first direction and the second direction when the geared body is in the second position; and a shaft extendable through the central bore and coupleable to the geared body to rotate therewith.

In Example 13, the subject matter of Example 12 optionally includes wherein each of the plurality of pawls are formed of the housing.

In Example 14, the subject matter of any one or more of Examples 12-13 optionally include wherein the plurality of pawls are each coupleable to the housing.

In Example 15, the subject matter of any one or more of Examples 12-14 optionally include the housing further comprising: a cap secured to the housing and extending distally into the central bore, the cap engageable with the geared body when the geared body is proximally translated, the cap comprising: a cap bore configured to receive the biasing element therein; and a cap boss disposed in the cap bore and extending distally, the cap boss extending into the biasing element to limit non-axial movement of the biasing element relative to the cap.

In Example 16, the subject matter of any one or more of Examples 12-15 optionally include the geared body further comprising: a geared body bore configured to receive the biasing element therein; and a geared body boss disposed in the geared bore and extending proximally, the geared boss extending into the biasing element to limit non-axial movement of the biasing element relative to the geared body.

In Example 17, the subject matter of Example 16 optionally includes a cap secured to the housing and extending distally into the central bore, the cap comprising: a cap tooth extending axially distally from the cap to engage the geared body when the geared body is proximally translated.

Example 18 is a method of installing a fastener using a ratcheting driver, the method comprising: engaging a fastener with a distal end of a shaft of the driver; applying a first torque to a handle in a first direction causing pawls to engage a geared body coupled to the shaft and rotating the shaft and the fastener in the first direction; applying a second torque to the handle in a second direction causing the pawls to disengage the geared body and allowing the handle to rotate relative to the geared body and the shaft in the second direction; and applying an axial force on the handle toward the fastener translating the geared body and causing teeth of the geared body to engage teeth of the handle so that the first torque applied to the handle causes rotation of the shaft in the first direction and the second torque applied to the handle causes rotation of the shaft in the second direction.

In Example 19, the subject matter of Example 18 optionally includes releasing the axial force allowing a biasing element to force the geared body away from the handle teeth such that the geared body teeth disengage the handle teeth.

In Example 20, the subject matter of Example 19 optionally includes applying the second torque to the handle after releasing the axial force, causing the pawls to disengage the geared body and allowing the handle to rotate in the second direction relative to the geared body and the shaft.

In Example 21, the driver, assembly, or method of any one of or any combination of Examples 1-20 is optionally configured such that all elements or options recited are available to use or select from.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

To secure fasteners to bones and prostheses, drivers, are often used. In some cases, ratcheting drivers may be preferred to avoid re-gripping of the driver during the procedure. Because the drivers are surgical instruments in contact with tissues and fluids of a patient, the drivers must be sterilized before they can be used in another surgery or operation. However, the process of sterilization can be labor-intensive and time-consuming (and therefore expensive). Because hospitals and physicians may seek to reduce tool costs, an inexpensive driver that is disposable is desired. The inventors have recognized, among other things, that to lower cost of the driver, fewer components can be used and plastic materials can be used.

The inventors have recognized that drivers comprised mostly of plastic components can include a geared body and pawls engaging the geared body to provide a ratcheting function. The inventors have further recognized that the driver can include a clutch interface to allow for transfer of torque from the handle to the fastener in either rotational direction, as desired. This design can enable a ratcheting mechanism for single-handed operation while the clutch provides a method for backing out a fastener, if necessary, without including a complex clutch of a reversible ratcheting system, for example.

Figure 1:
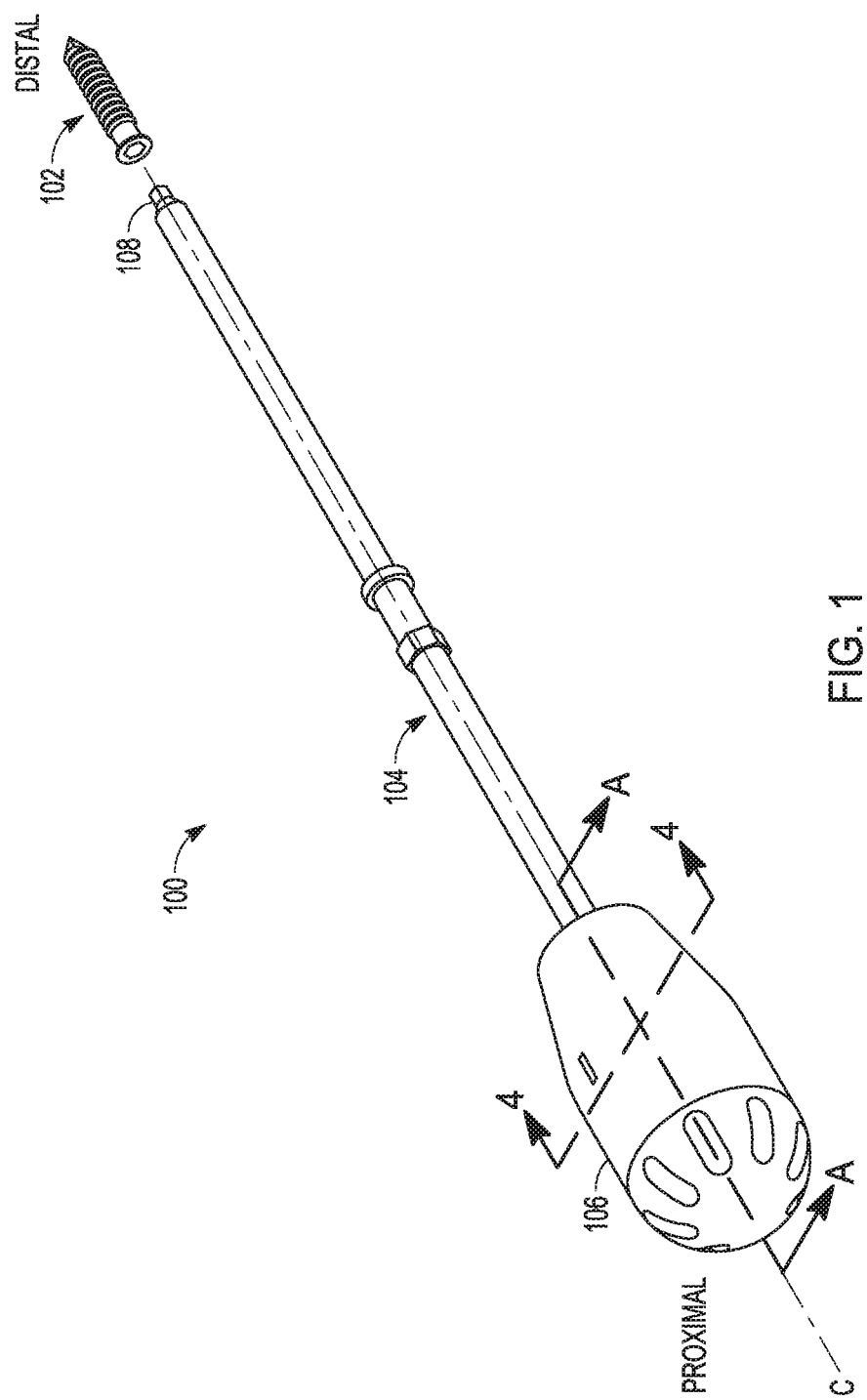
FIG. 1 illustrates an isometric view of a driver, in accordance with at least one example of this disclosure.

FIG. 1 illustrates an isometric view of driver 100, in accordance with at least one example of this disclosure. Driver 100 can include shaft 104 and handle 106. Shaft 104 can include tool interface 108. Also shown in FIG. 1 is fastener 102, axis C, and orientation indicators Proximal and Distal.

Handle 106 can be a rigid member comprised of plastics, metals, composites, combinations thereof, and the like. Handle 106 can be sized and shaped to be grasped and rotated. Handle 106 can be coupled to shaft 104 at a distal portion of handle 106, as described below in further detail.

Shaft 104 can be a rigid elongate member comprised of plastics, metals, composites, combinations thereof, and the like. Shaft 104 can be coupled to handle 106, as described above, and can be configured to engage fastener 102 at a distal termination of shaft 104, such that a torque applied to handle 106 can be transferred through shaft 104 to fastener 102. Tool interface 108 can be hexagonal, standard, cross-recess, and the like, configured to matingly engage fastener 102.

Fastener 102 can be a fastener configured to secure to a work piece, such as a bone, plate, prosthesis, or other device used in a surgery or operation. In other examples, fastener 102 can be configured to engage wood, plastics, metals, and the like, for applications outside of surgical procedures. Fastener 102 can be comprised of plastics, metals, composites, combinations thereof, and the like. In some examples, fastener 102 can include a head configured to interface with a tool or driver.

In operation of one example, handle 106 can be grasped by a user, such as a physician, and tool interface 108 of shaft 104 can be inserted into a head of fastener 102. The user can then apply a torque to handle 106 about longitudinal axis C. Handle 106 can transfer the torque to fastener 102 via shaft 104 to turn fastener 102, which can drive the fastener into the work piece or can remove the fastener therefrom. In some examples, handle 106 can include a ratcheting mechanism configured to transfer a torque from handle 106 to shaft 104 in one rotational direction and not the other. In some examples, driver 106 can include a clutch that is selectively engageable allowing torque be transferred from handle 106 to shaft 104 in either rotational direction when engaged. Both of these features, discussed below in further detail, can increase operational efficiency by reducing a need to re-grasp and enabling single-hand operation of driver 100.

Figure 2A:
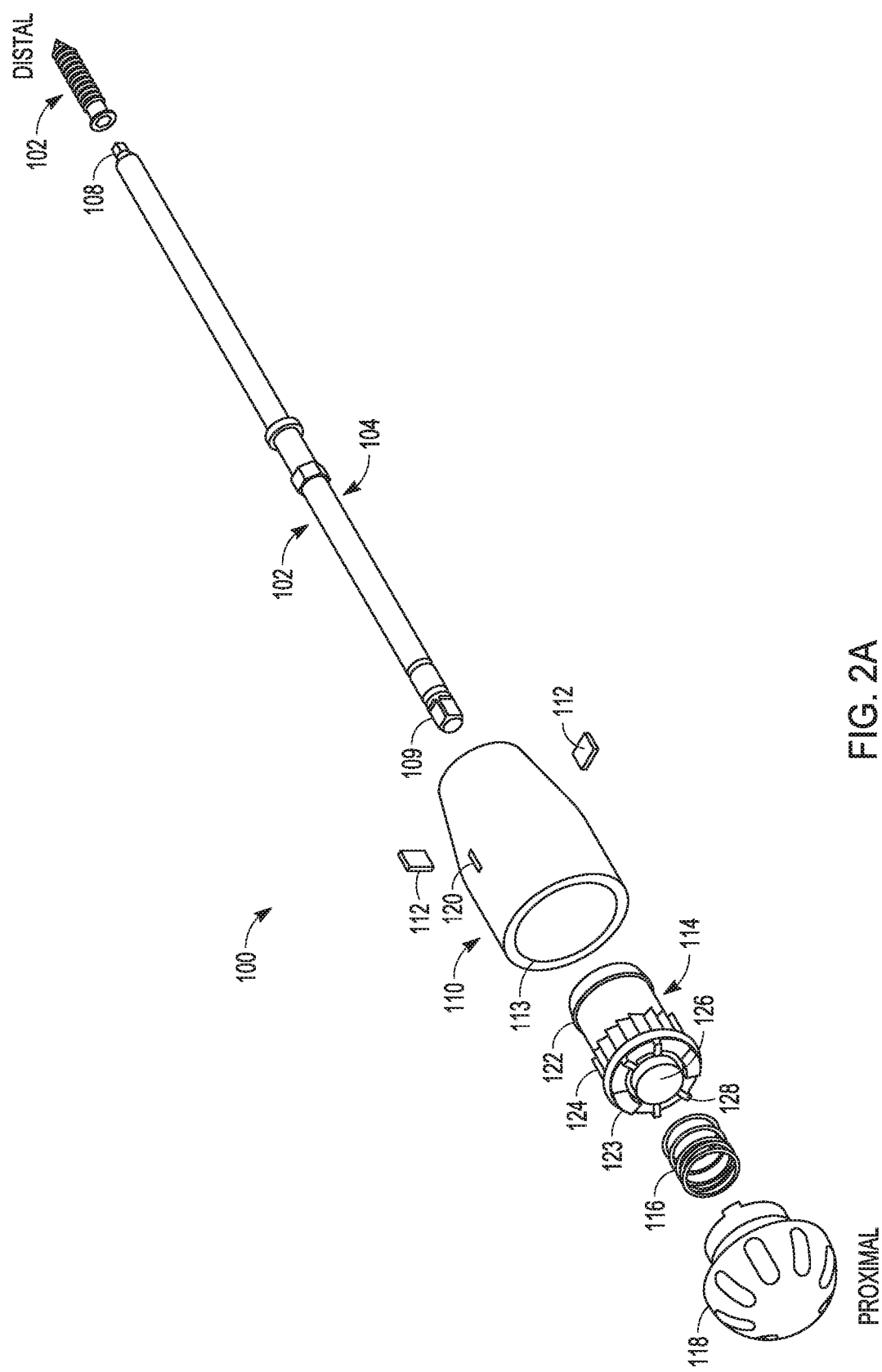
FIG. 2A illustrates an exploded view of a driver from a proximal perspective, in accordance with at least one example of this disclosure.
Figure 2B:
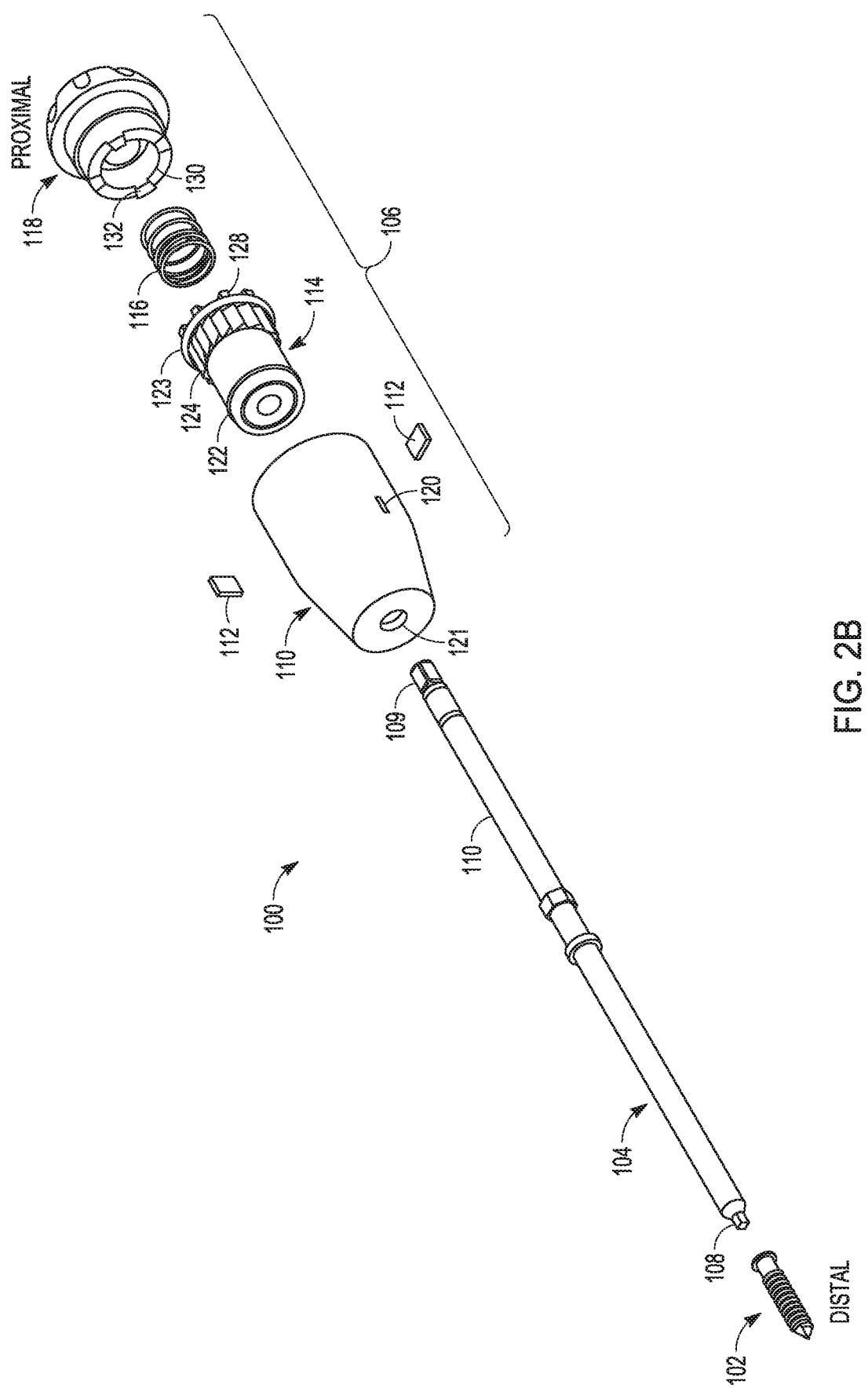
FIG. 2B illustrates an exploded view of a driver from a distal perspective, in accordance with at least one example of this disclosure.

FIG. 2A illustrates an exploded view of driver 100 from a proximal perspective, in accordance with at least one example of this disclosure. FIG. 2B illustrates an exploded view of driver 100 from a distal perspective, in accordance with at least one example of this disclosure. FIGS. 2A and 2B are discussed below concurrently.

Driver 100 can include shaft 104 and handle 106. Shaft 104 can include tool interface 108 and proximal connector 109. Handle 106 can include housing 110, pawls 112, geared body 114, biasing element 116, and cap 118. Housing 120 can include central bore 113, pawl slots 120 (only 1 visible in FIG. 2A and only 1 visible in FIG. 2B), and shaft bore 121. Geared body 114 can include distal guide 122, proximal guide 123, geared portion 124, boss 126, and teeth 128. Cap 118 can include cap bore 130 (shown in FIG. 2B only) and teeth 132 (shown in FIG. 2B only).

Housing 110 can be a rigid member comprised of materials such as metals, plastics, composites, combinations thereof, and the like. Housing 110 can have a tapered cylindrical shape in some examples and can have other shapes, such as regular and irregular prismatic geometric shapes in other examples. Housing 110 can include central bore 113, which can be an axial bore extending from a proximal portion of housing 110, coaxial with axis C, and can terminate at a distal portion of housing 110, creating a cavity within housing 110. Housing 110 can also include shaft bore 121, which can be an axial bore that can be co-axial with central bore 113 and can extend from a distal end of housing 110 therein. Central bore 113 can be sized to retain geared body 114, as discussed below, and shaft bore 121 can be sized to receive shaft 104 therethrough, as discussed further below. Pawl slots 120 can be circumferentially spaced around housing 110 and can each extend radially through housing 110 and into central bore 113. Each of pawl slots 120 can be sized to receive one of pawls 112 therethrough, in some examples.

Pawls 112 can be rigid or semi-rigid members comprised of materials such as metals, plastics, composites, combinations thereof, and the like. Pawls 112 can be secured to housing 110 and can extend through pawl slots 120 radially into central bore 113. In some examples, pawls 112 can be formed into housing 110 such that housing 110 and pawls 112 can be a single piece or component.

Geared body 114 can be a rigid element disposable within central bore 113 of housing 110. Geared body 114 can be a rigid or semi-rigid member comprised of materials such as metals, plastics, composites, combinations thereof, and the like. In some examples, geared body 14 can include an assembly of multiple components and in some examples, can be a single component fabricated using a molding process or a three dimensional printing process.

Distal guide 122 can be a circumferential portion of geared body 114 distally located on geared body 114 and having a relatively small height or length. Distal guide 122 can extend slightly radially from a radial outer circumferential surface of geared body 114. Proximal guide 123 can be similarly configured to distal guide 122 but can be proximally located on geared body 114.

Geared portion 124 can include gears configured to interface with pawls 112, as described in further detail below. The gears can extend radially from geared body and can be spaced from each other, as described in further detail below. Boss 126 can be a proximal portion of geared body 114 extending axially therefrom and sized to be receive and retain biasing element 116. Teeth 128 can be disposed radially outward of boss 126 and can extend axially from geared body 114.

Cap 118 can be a rigid member comprised of materials such as metals, plastics, composites, combinations thereof, and the like. Cap 118 can have a shape complimentary to housing 110 and can be configured to secure within a distal portion of housing 110. Cap bore 130 (shown in FIG. 2B only) can extend proximally into cap 118 and can be sized to receive and retain biasing element 116. Teeth 132 (shown in FIG. 2B only) can be disposed radially outward of cap bore 130 and can extend axially from cap 118. Cap teeth 132 and geared body teeth 128 can be configured to selectively interface, as described further below.

Biasing element 116 can be a resilient element such as a compression coil spring, in some examples, and can be other springs or resilient members, such as a wave spring or compressible and resilient members comprised of materials such as rubbers, plastic, and the like.

Operation of the components of driver 100 are discussed below with respect to FIG. 3.

Figure 3:
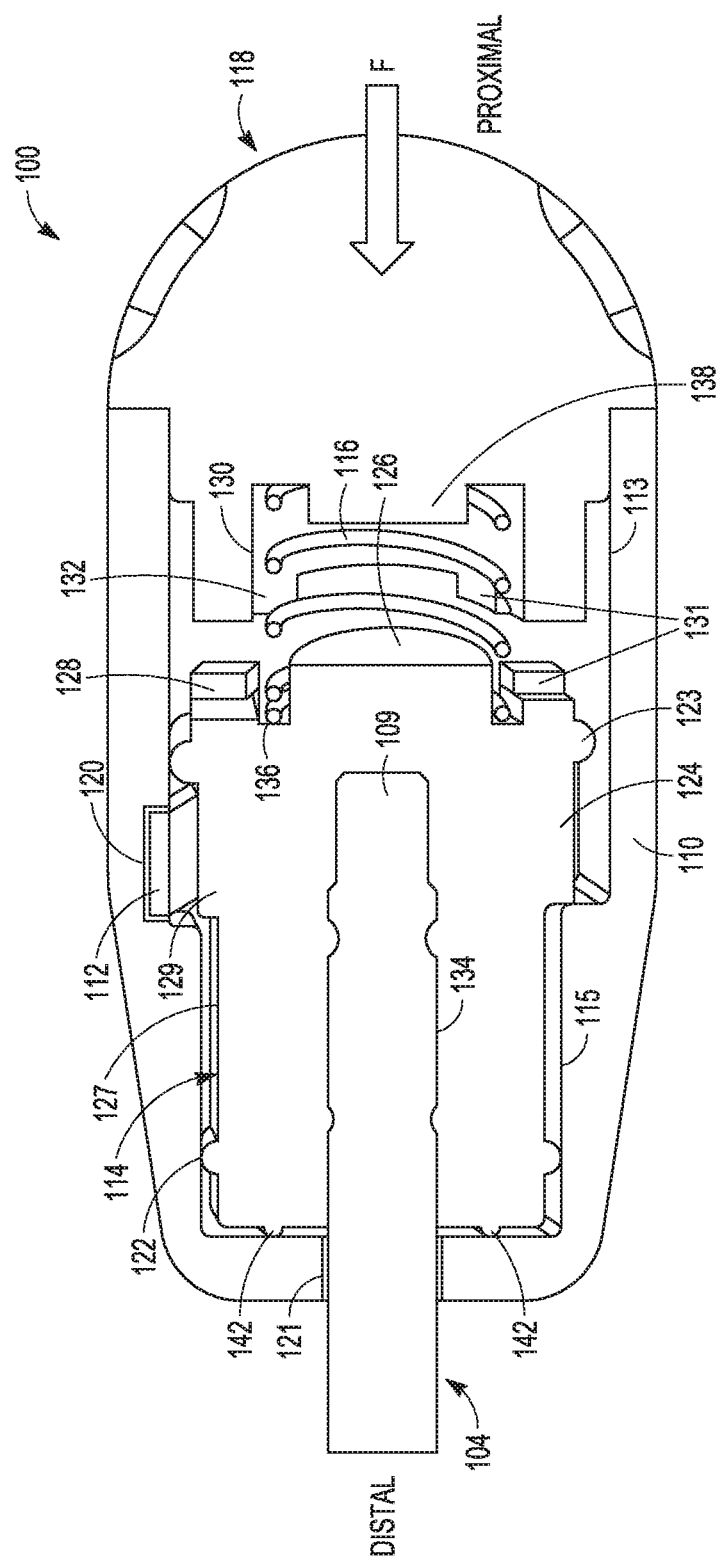
FIG. 3 illustrates a cross-sectional view of a driver across indicators A-A of FIG. 1, in accordance with at least one example of this disclosure.

FIG. 3 illustrates a cross-sectional view of driver 100 across indicators A-A of FIG. 1, in accordance with at least one example of this disclosure. Shaft 104 and handle 106 can be consistent with the description of FIGS. 1-2B discussed above; however, FIG. 3 shows additional details of how shaft 104 and handle 106 can connect and operate together.

For example, FIG. 3 shows shaft bore 134 of geared body 114, which can extend from a distal portion of geared body 114 proximally into geared body 114 and can terminate prior to exiting a proximal portion of geared body 114. Shaft bore 134 can be coaxial with shaft bore 121 of housing 110 and can be sized to receive and retain shaft 104 within geared body 114 in a snap-fit configuration, in some examples. In other examples, geared body 114 and shaft 104 can be formed of a single piece via a molding or three dimensional printing operation, in some examples. In some examples, proximal connector 109, which can have a square prismatic geometric shape (as shown in FIGS. 2A and 2B), can be received by a proximal portion of shaft bore 134 which can have a complimentary shape to prevent rotation of shaft 104 relative to shaft bore 134 and therefore geared body 114.

Geared body 114 can also include geared body groove 136, which can be a circumferential groove disposed around a distal base of geared body boss 126. Geared body groove 136 can be sized to retain therein a distal portion of biasing element 116. Geared body 114 can further include end spacer 142, which can be a circumferential extension of geared body extending distally from a distal end of geared body 114 and can have a relatively small radial thickness to minimize surface contact between end spacer 142 and housing 110.

Cap 118 can further include cap boss 138, which can be a boss disposed in cap bore 130, in some examples, and can be configured to extend distally from a proximal portion of cap 118, and can terminate within cap bore 130. Cap boss 138 can be sized to receive biasing element 116 thereon, to retain biasing element 116 within cap bore 130 and to help prevent non-axial rotation of biasing element 116.

FIG. 3 also shows that housing 110 can include two bores, central bore 113 and distal central bore 115 (which can be a counter-bore to central bore 113), where central bore 113 can have a diameter that is larger than distal central bore 115. Additionally, housing 110 can include undercut 140, which can be a transverse surface of housing 110 formed at the intersection of central bore 113 and distal central bore 115.

Similarly, geared body can include distal portion 127 and proximal portion 129, where proximal portion 129 has a larger diameter than distal portion 127. In operation of some examples, contact between a distal end of proximal portion 129 and undercut 140 can limit distal translation of geared body 114, together with end spacer 142.

FIG. 3 also shows how geared body boss 126 and cap boss 138 retain biasing element 116. Also, FIG. 3 shows distal guide 122 in contact with distal central bore 115 and shows proximal guide 123 in contact with central bore 113, such that distal guide 122 and proximal guide 123 maintain desired radial positions of geared body 114 within housing 110 (central bore 113 and distal central bore 115) while limiting contact between geared body 114 and housing 110.

In operation of some examples, a user can engage a fastener (such as fastener 102 of FIG. 1) with a distal portion of shaft 104. The user can apply a torque in a first direction to rotate housing 110, which can rotate pawls 112. Pawls 112 can engaged geared body 114 to rotate in the same direction (as discussed below with respect to FIG. 4). As geared body 114 rotates, so too does shaft 104. Shaft 104 can transfer the torque to the fastener, allowing the fastener to be rotated into the work piece. If body 110 is rotated in the opposite (second) direction, pawls 112 will not rotate geared body 114 and housing 110 can therefore spin relative to geared body 114, allowing a user to reset a hand position to then apply torque in the first direction, generally operating driver 100 in a ratcheting fashion, and enabling efficient single-hand operation of driver 100.

In some examples, it may be desired to apply a torque to shaft 104 and to fastener 102 in the second direction (for example to remove fastener 102 from a workpiece). In such examples, a user can apply an axial force in direction F (as shown in FIG. 3), which can be opposed by biasing element 116, which biases geared body 114 axially toward the distal portion of housing 110. When the force is larger than the force applied by biasing element 116 (when the distal portion of shaft 104 is constrained from moving axially), housing 110 can move in the direction F, such that cap 118 moves towards geared body 114. As cap 118 engages geared body 114, geared body teeth 128 can align with cap teeth 132 such that radial surfaces of cap teeth 132 can engage radial surfaces of geared body teeth 128 when housing 110 is rotated about its axis in either rotational direction. When geared body teeth 128 and cap teeth 132 are engaged, torque can be transferred from housing 110 to geared body 114 in either direction, allowing a user to selectively rotate the fastener in either the first or second direction about the axis of driver 100. When the user desires to return to the ratcheting function of driver 100 described above, the axial force in the direction of F can be removed (or reduced below the force of biasing element 116), allowing biasing element to force geared body 114 distally (generally axially), separating geared body teeth 128 and cap teeth 130. Both geared body teeth 128 and cap teeth 130 can include radially extending edges 131, in some examples, to maximize surface area contact between geared body teeth 128 and cap teeth 130.

Because driver 100 only ratchets in a single direction, fewer components can be used, reducing cost of driver 100. By including selective engagement between cap teeth 132 and geared body teeth 128, driver 100 can maintain functionality of transferring torque in either rotational direction about an axis of the driver. Both functions allow simple and efficient single-handed operation of driver 100. Further, by constructing many of the components of driver 100 out of lower-cost materials (such as plastics) and by forming components together (such as pawls 112 into housing 100), the cost of driver 100 can be further reduced.

Figure 4:
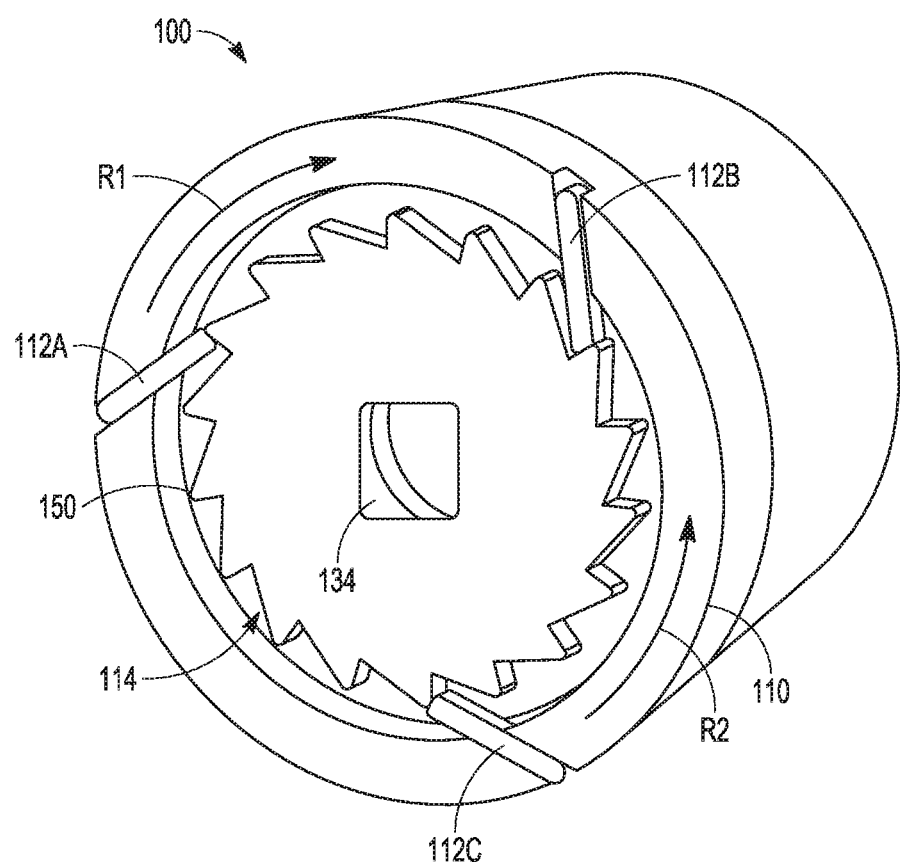
FIG. 4 illustrates a cross-sectional view of a driver across indicators 4-4 of FIG. 1, in accordance with at least one example of this disclosure.

FIG. 4 illustrates a cross-sectional view of driver 100 across indicators 4-4 of FIG. 1, in accordance with at least one example of this disclosure. FIG. 4 can be consistent with FIGS. 1-3 discussed above, but can further show gear teeth 150 of geared body 114 and three of pawls 112 (112A, 112B, and 112C). Also shown in FIG. 4 are rotational directions R1 and R2.

Geared body 114 can include gear teeth 150, which can have radial faces configured to engage pawls 112 when housing 110 is rotated in first rotational direction R1. Each gear tooth 150 can also include an angled or arcuate face opposite the transverse face configured to allow pawls 112 to pass over geared body 114 when housing 110 is rotated in second rotational direction R2, providing a ratcheting interface between housing 110 and geared body 114. In operation, torque applied to housing 110 in the direction of first rotational direction R1 can be transferred from housing 110 to geared body 114 through pawls 112, but torque applied to housing 110 in second rotational direction R2 cannot be so transferred, because pawls cannot engage teeth 150 of geared body 114 to transfer such torque.

FIG. 4 further shows how shaft bore 134 of geared body 114 can have a square prismatic geometric shape to interface with proximal connector 109 of shaft 104 to help prevent rotation of shaft 104 relative to geared body 114.

In some examples, there can be one of pawls 112. In other examples, there can be 2, 3, 4, 5, 6, 7, 8, 9, 10 and the like. In some examples, there can be three of pawls 112 (112A, 112B, and 112C), as shown in FIG. 4.

Figure 5:
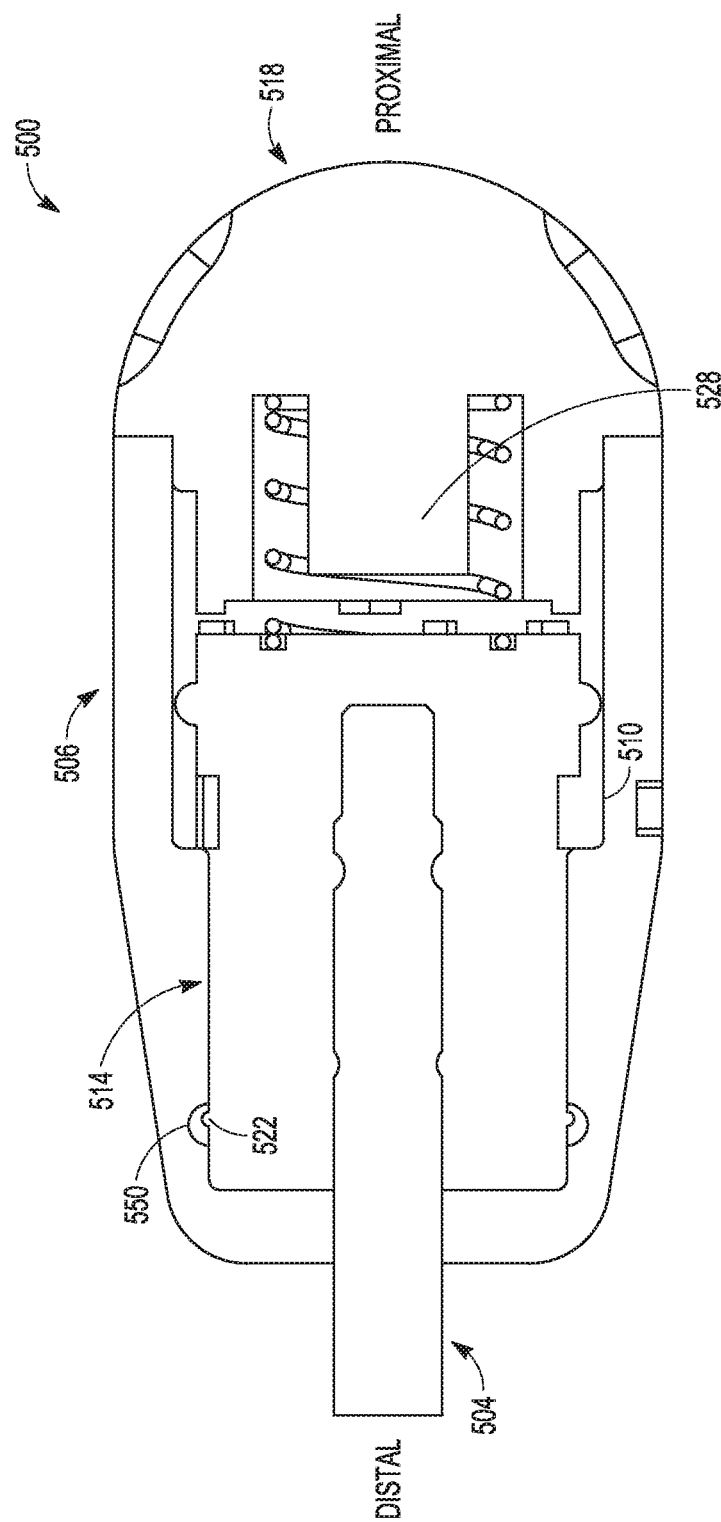
FIG. 5 illustrates another driver from a similar perspective of the cross-sectional view indicated by indicators A-A of FIG. 1, in accordance with at least one example of this disclosure.

FIG. 5 illustrates driver 500 from a similar perspective of the cross-sectional view indicated by indicators A-A of FIG. 1, in accordance with at least one example of this disclosure. Driver 500 can include shaft 504, handle 506, geared body 514, biasing element 516, and cap 518.

Driver 500 can be similar to driver 100 discussed above, except that cap boss 538 of cap 518 of driver 500 can be relatively large, extending most of the axial distance of the cap bore. Driver 500 can also differ in that housing 510 can include retaining groove 550, which can be sized to retain distal guide 522 therein while still allowing geared body 114 to translate axially within housing 110 allowing cap teeth and geared body teeth to engage and disengage as desired.

Figure 6:
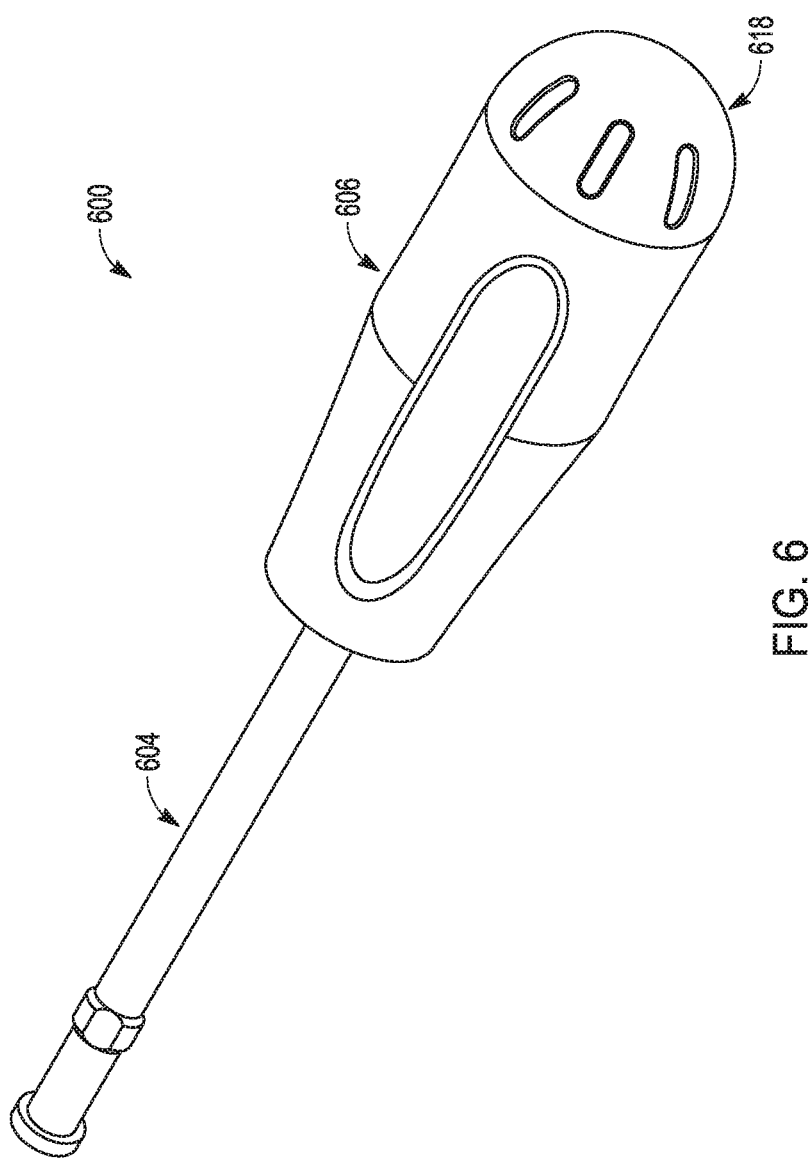
FIG. 6 illustrates an isometric view of a driver, in accordance with at least one example of this disclosure.

FIG. 6 illustrates an isometric view of driver 600, in accordance with at least one example of this disclosure. Driver 600 can include shaft 604, handle 606, and cap 618. Shaft 604 can be rigidly coupled to handle 606, in some examples, such that handle 606 cannot be rotated relative to shaft 604. Cap 618 can be coupled to handle 606 (for example, in a snap configuration), such that cap 618 can be rotated relative to handle 606 and therefore relative to shaft 604 allowing a position of driver 600 to be maintained while a hand is turned, improving single-handed operation of driver 600.

Figure 7:
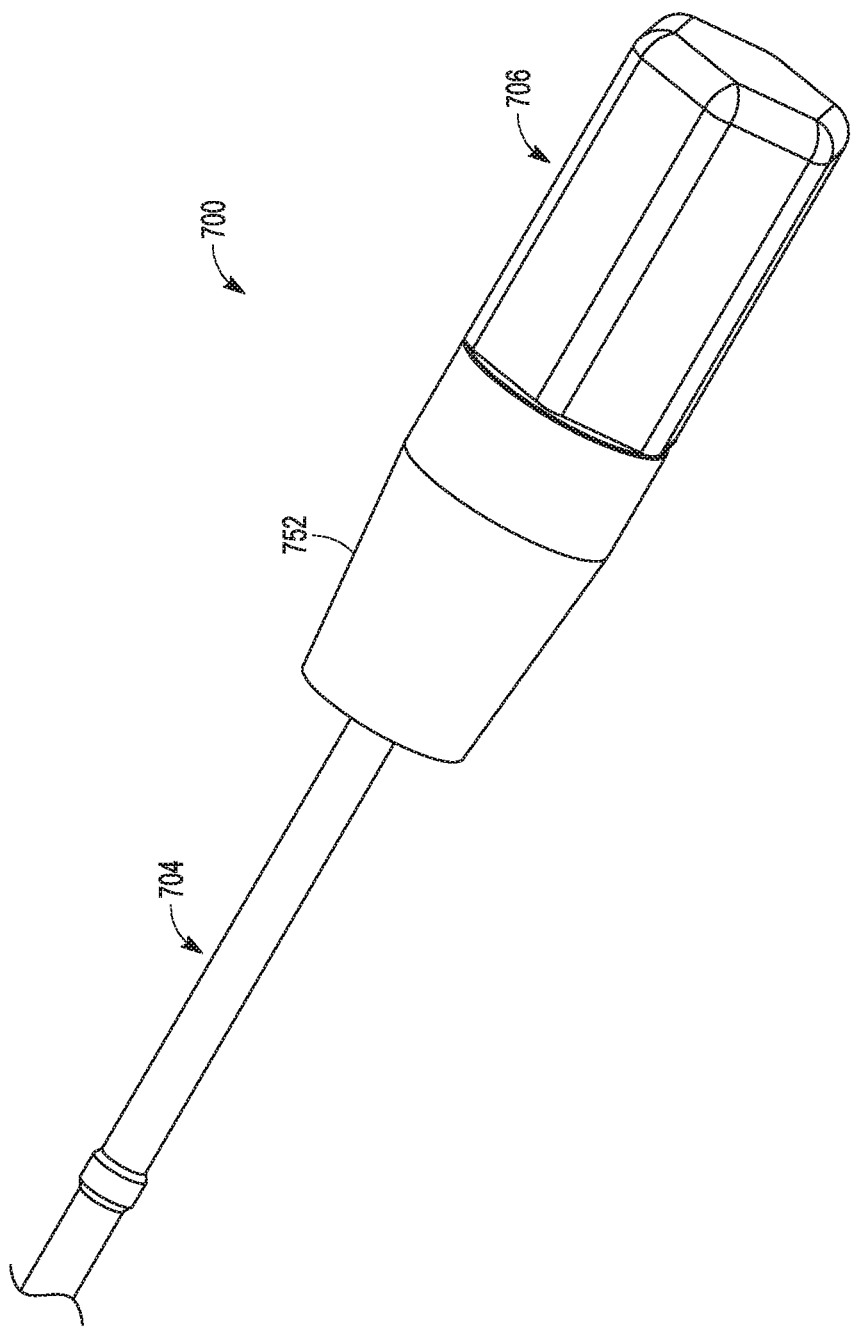
FIG. 7 illustrates an isometric view of a driver, in accordance with at least one example of this disclosure.

FIG. 7 illustrates an isometric view of driver 700, in accordance with at least one example of this disclosure. Driver 700 can include shaft 704, handle 706, and collar 752. Shaft 704 can be rigidly coupled to handle 706, in some examples, such that handle 706 cannot be rotated relative to shaft 704. Collar 752 can receive shaft 704 therethrough without coupling to shaft 704. Collar 752 can be coupled to handle 706 (for example, in a snap configuration), such that collar 752 can be rotated relative to handle 706 and therefore relative to shaft 704 allowing a position of driver 700 to be maintained with one hand while a second hand turns handle 706 and/or re-grips handle 706, improving two-handed operation of driver 700. In some examples, collar 752 can be mounted to handle 106 of FIGS. 1-4.

Figure 8:
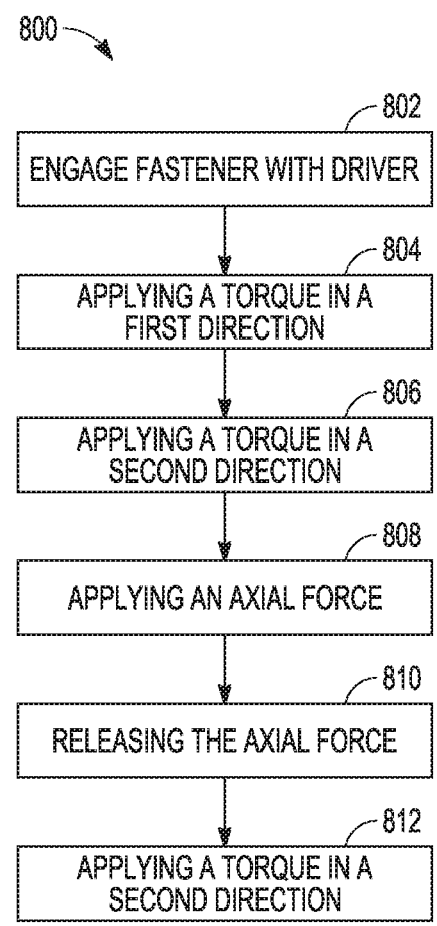
FIG. 8 illustrates a schematic of a method, in accordance with at least one example of this disclosure.

FIG. 8 illustrates a schematic of method 800, in accordance with at least one example of this disclosure. The steps or operations of method 800 are illustrated in a particular order for convenience and clarity; many of the discussed operations can be performed in a different sequence or in parallel without materially impacting other operations. Method 800 as discussed includes operations performed by multiple different actors, devices, and/or systems. It is understood that subsets of the operations discussed in method 800 attributable to a single actor, device, or system could be considered a separate standalone process or method. At step 802, method 800 can begin with step 802 where fastener 102 can be engaged by shaft 104 of driver 100.

At step 804 a first torque can be applied to handle 106 in a first direction causing pawls 112 to engage geared body 114 (which can be coupled to shaft 104) and rotate shaft 104 and fastener 102 in the first direction. At step 806, a second torque can be applied to handle 106 in a second direction causing pawls 112 to disengage geared body 114 and allowing handle 106 to rotate relative to geared body 114 and shaft 104 in the second direction. Then, when it is desired to transfer torque applied in a second direction from handle 106 to shaft 104, step 808 can be performed, where an axial force can be applied to handle 106 toward the fastener. The axial force can cause geared body 114 to translate, which can cause geared body teeth 128 to engage cap teeth 132 (coupled to handle 106 via cap 118) so that the first torque applied to handle 106 causes rotation of shaft 104 in the first direction and the second torque applied to handle 106 causes rotation of shaft 104 in the second direction.

At step 810, the axial force can be released, allowing biasing element 116 to force geared body 114 away from handle teeth 132 such that geared body teeth 128 disengage handle teeth 132. At step 812, the second torque can again be applied to handle 106 after releasing the axial force, causing pawls 112 to disengage geared body 114 and allowing handle 106 to rotate in the second direction relative to geared body 114 and shaft 104.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A ratcheting driver configured to selectively transmit a torque to a fastener, the driver comprising:
   a handle comprising:
      a housing including a central bore and a shaft bore extending through a distal portion of the housing;
      a pawl extending radially inward from the housing into the central bore; and
      a biasing element engaging the housing;

a geared body rotatably engageable with the pawl to allow rotation of the geared body relative to the handle in a first direction and to limit rotation of the geared body relative to the handle in a second direction, the biasing element engageable with the geared body to bias the geared body distally, the geared body proximally translatable within the handle to engage the handle to limit rotation of the geared body relative to the handle in the first direction and the second direction; and a shaft extendable through the shaft bore and coupleable to the geared body and rotatable therewith, the shaft configured to interface with a fastener.

2. The driver of claim 1, wherein the pawl is formed into a radially inner portion of the housing.

3. The driver of claim 1, the handle further comprising:
a cap secured to the housing and extending distally into the central bore, the cap engageable with the geared body when the geared body is proximally translated, the cap comprising:
   a cap bore configured to receive the biasing element therein; and
   a cap boss disposed in the cap bore and extending distally, the cap boss extending into the biasing element to limit non-axial movement of the biasing element relative to the cap.

4. The driver of claim 1, the geared body further comprising:
a geared body bore configured to receive the biasing element therein; and
a body boss disposed in the geared bore and extending proximally, the body boss extending into the biasing element to limit non-axial movement of the biasing element relative to the geared body.

5. The driver of claim 1, the handle further comprising:
a cap secured to the housing and extending distally into the central bore, the cap comprising:
   a cap tooth extending distally from the cap to engage the geared body when the geared body is proximally translated.

6. The driver of claim 5, the geared body further comprising:
a geared body tooth extending proximally from the geared body to engage the cap when the geared body is proximally translated and to engage the cap tooth to prevent the geared body from rotating relative to the handle.

7. The driver of claim 6, wherein:
the geared body tooth includes a plurality of geared body teeth, each geared body tooth including radially extending edges.

8. The driver of claim 1, the geared body further comprising:
a guide extending radially from a distal portion of the geared body to engage a radially internal wall of the body of the handle to prevent non-axial translation of the geared body.

9. The driver of claim 1, further comprising:
a collar coupleable to proximal portion of the handle and rotatable relative to the handle and the shaft.

10. The driver of claim 1, wherein the pawl is coupleable to the housing.

11. The driver of claim 1, wherein:
the central bore further comprises a distal portion having a distal bore diameter and a proximal portion having a proximal bore diameter that is larger than the distal bore diameter; and the geared body further comprises a distal portion having a distal geared body diameter that is smaller than the distal bore diameter, and a proximal portion having a proximal geared body diameter that is larger than the distal geared body diameter, larger than the distal bore diameter and smaller than the proximal bore diameter so that distal translation of the geared body is limited by contact between the proximal portion of the geared body and an undercut formed between distal portion and proximal portion of the central bore.

12. A ratcheting driver configured to selectively transmit a torque to a fastener, the driver comprising:
a housing including a central bore;
a plurality of pawls extending radially from the housing into the central bore;
a biasing element engaging the housing;
a geared body translatable within the housing between a first position and a second position and rotatably engageable with the plurality of pawls to allow rotation of the geared body relative to the housing in a first direction and to limit rotation of the geared body relative to the housing in a second direction when the geared body is in the first position, the biasing element engageable with the geared body to bias the geared body to the first position, and the geared body engageable with the housing to limit rotation of the geared body relative to the housing in the first direction and the second direction when the geared body is in the second position; and
a shaft extendable through the central bore and coupleable to the geared body to rotate therewith.

13. The driver of claim 12, wherein each of the plurality of pawls are formed of the housing.

14. The driver of claim 12, wherein the plurality of pawls are each coupleable to the housing.

15. The driver of claim 12, the housing further comprising:
a cap secured to the housing and extending distally into the central bore, the cap engageable with the geared body when the geared body is proximally translated, the cap comprising:
   a cap bore configured to receive the biasing element therein; and
   a cap boss disposed in the cap bore and extending distally, the cap boss extending into the biasing element to limit non-axial movement of the biasing element relative to the cap.

16. The driver of claim 12, the geared body further comprising:
a geared body groove configured to receive the biasing element therein; and
a geared body boss disposed in the geared bore and extending proximally, the geared boss extending into the biasing element to limit non-axial movement of the biasing element relative to the geared body.

17. The driver of claim 16, further comprising: a cap secured to the housing and extending distally into the central bore, the cap comprising: a cap tooth extending axially distally from the cap to engage the geared body when the geared body is proximally translated, a geared body tooth extending axially proximally from the geared body to engage the cap when the geared body is proximally translated and to engage the cap tooth to prevent the geared body from rotating relative to the handle, the geared body tooth including radially extending edges.

18. A method of installing a fastener using a ratcheting driver, the method comprising:

engaging a fastener with a distal end of a shaft of the driver;

applying a first torque to a handle in a first direction causing pawls to engage a geared body coupled to the shaft and rotating the shaft and the fastener in the first direction;

applying a second torque to the handle in a second direction causing the pawls to disengage the geared body and allowing the handle to rotate relative to the geared body and the shaft in the second direction; and applying an axial force on the handle toward the fastener translating the geared body and causing teeth of the geared body to engage teeth of the handle so that the first torque applied to the handle causes rotation of the shaft in the first direction and the second torque applied to the handle causes rotation of the shaft in the second direction.

19. The method of claim 18 further comprising:

releasing the axial force allowing a biasing element to force the geared body away from the handle teeth such that the geared body teeth disengage the handle teeth.

20. The method of claim 19 further comprising:

applying the second torque to the handle after releasing the axial force, causing the pawls to disengage the geared body and allowing the handle to rotate in the second direction relative to the geared body and the shaft.

* * * * *